United States Patent [19]

Warnke

[11] Patent Number: 5,725,558
[45] Date of Patent: Mar. 10, 1998

[54] DEVICE FOR INFLUENCING LOW-FREQUENCY ELECTRICAL AND MAGNETIC FIELDS

[75] Inventor: Ulrich Warnke, Scheidt, Germany

[73] Assignee: Dr. Fischer Aktiengesellschaft, Vaduz, Liechtenstein

[21] Appl. No.: 256,636

[22] PCT Filed: Nov. 9, 1993

[86] PCT No.: PCT/EP93/03126

§ 371 Date: Jul. 15, 1994

§ 102(e) Date: Jul. 15, 1994

[87] PCT Pub. No.: WO94/11062

PCT Pub. Date: May 26, 1994

[30] Foreign Application Priority Data

Nov. 17, 1992 [DE] Germany .......... 42 38 829.5

[51] Int. Cl.[6] ................................................ A61N 2/00
[52] U.S. Cl. .................................. 607/3; 607/1; 607/2
[58] Field of Search ...................................... 607/1–3

[56] References Cited

U.S. PATENT DOCUMENTS

| | | | |
|---|---|---|---|
| 4,454,883 | 6/1984 | Fellus | 607/3 |
| 4,622,952 | 11/1986 | Gordon | 600/4 |
| 4,685,462 | 8/1987 | Olsen | 607/98 |
| 5,058,582 | 10/1991 | Thaler | 607/2 |
| 5,123,413 | 6/1992 | Hassegawa et al. | 607/2 |

FOREIGN PATENT DOCUMENTS

| | | | |
|---|---|---|---|
| 393084 | 9/1987 | Austria . | |
| 130474A | 1/1985 | European Pat. Off. | 607/2 |
| 0181053 | 5/1986 | European Pat. Off. . | |
| 0217011 | 4/1987 | European Pat. Off. . | |
| 0377284 | 7/1990 | European Pat. Off. . | |
| 3327166 | 4/1984 | Germany | 607/2 |
| 9218873 | 10/1992 | WIPO . | |

Primary Examiner—William E. Kamm
Assistant Examiner—Carl H. Layno
Attorney, Agent, or Firm—Robert W. Becker & Associates

[57] ABSTRACT

A device for influencing localized low-frequency electric and magnetic fields which act on a conductive structure located within a delimited space, in particular an organic substance such as a living organism, compensates the localized fields by the establishment of an interference field. With such an interference field it is possible to eliminate the disruptive influence of localized fields as well as to provide a possibility for imposing a desired influence.

49 Claims, 5 Drawing Sheets

DEVICE FOR INFLUENCING LOW-FREQUENCY ELECTRICAL AND MAGNETIC FIELDS

BACKGROUND OF THE INVENTION

The invention concerns a device for influencing localized low-frequency electric and magnetic fields which act on a conductive structure located within a delimited space, such as the organic structure of a living organism. Such fields are predominantly caused by high voltage power lines, railway power lines and domestic power supply lines, as well as the electric units connected thereto.

As has been known for some time that low-frequency electric and magnetic fields have a considerable influence on organic structures, and they do so by means of their effect on biological processes. One of the causes is the influence on ions within these conductive structures. In order to avoid repetition, this topic is dealt with as part of the explanation of the invention. In this context, the important feature is frequently not just the field of the fundamental wave of the fields, but also its harmonics. A spectral observation indicates frequencies referred to as concentration frequencies which are determined by the fundamental wave and the harmonics. Generally speaking, only harmonics of up to the third order are of interest.

It is an object of the invention to reduce at least to a considerable degree the effect of such fields within a delimited space and at the same time to provide a targeted effect on a substance.

SUMMARY OF THE INVENTION

This is achieved according to the invention with a device for influencing localized low-frequency electric and magnetic alternating fields which act on a conductive structure located within a delimited space, such as the organic substance of a living organism, which device has a receiving device which picks up the fields within the delimited space in the form of field components oriented according to a system of coordinates such as a Cartesian system, from which are then derived the fields used for compensating the alternating fields, by providing a measuring device that is connected to the receiving device, which measuring device is used for determining amplitude, frequency and orientation of the field components picked up by the receiving device, by providing a transmitter, comprising a device for generating a counter field in the delimited space and connected to the measuring device by means of a control element, by providing the control element, the transmitter and the device which generates the opposite field so as to be adjustable in accordance with the measured values from the measuring device in their frequencies, strengths and counter field coordinate orientations such that the counter field generated in the delimited space interferes with the localized fields in such a way as to compensate at least approximately their effects on the conductive structure. The transmitter either generates with the device for generating the counter field a further oscillation field with a frequency lower than that of the counter field for compensating the localized fields having the same concentration frequency, in particular an oscillation field with a frequency between approximately 1 Hz and approximately 8 Hz or approximately 10 Hz and approximately 30 Hz, or the frequency of the transmitter is displaced in relation to the concentration frequency of the localized fields by such a value as to cause an interference oscillation to be generated within the delimited space, whereby the interference oscillation is of a relatively low frequency in relation to the concentration frequency of the localized fields, in particular, has a frequency between approximately 1 Hz and approximately 8 Hz or approximately 10 Hz and approximately 30 Hz.

Devices for compensating disruptive magnetic fields are generally known, as are devices for compensating frequencies from the electric power supply network, for example, from DE-OS 32 07 708 A1 and DE-OS 32 09 453 A1. These devices operate three-dimensionally with respect to compensating effects and use, among other elements, Helmholtz coils. However, they lack the characteristic features of the present invention. This is also the case with the device described in AT 393 084 B for neutralization of the influences of geological factors or disruptive zones. DE-OS 41 01 481 A1 and PCT application Wo 92/18873 describe the compensation of disruptive magnetic fields in devices used for measuring nuclear magnetic resonance or electron spin resonance.

It is advantageous to equip the device with a frequency filter, in particular a low-pass filter, which restricts evaluation to the field components of the localized fields because this provides an effective prevention against self-excitation of the device. This can also be achieved by providing a loop circuit which monitors the adjustment of the control member briefly at regular intervals in accordance with specified frequency criteria, and which, given compliance, decouples the transmitter from the receiving device.

In a further development of the invention, a second receiving device is provided in order to determine the constant magnetic field present within the delimited space, and in particular, the strength and orientation of coordinates of the geomagnetic field. Furthermore, a device is provided to which are sent the signals from the first and second receiving devices and which is used for determining the resonances occurring within the conductive structure It is also advantageous to design a device in accordance with the invention in such a way that the frequencies of the interference oscillation and the transmitter power can be set at high enough levels as a function of the geomagnetic field, so that the interference oscillation in cooperation with the constant magnetic field fulfills the conditions for a cyclotron resonance with ions, in particular calcium ions ($Ca^{++}$), potassium ions ($K^+$) or sodium ions ($Na^+$), or for nuclear magnetic resonance (NMR) of an organic substance.

It has proved advantageous to provide the device with a receiving device that picks up the field components in Cartesian coordinates and to design the receiving device such that, for each coordinate direction, one receiving unit is provided for the electric field components and one for the magnetic field components, that these receiving units are connected to the inputs of a multiplexer, and that the multiplexer output, in a preferred embodiment, is connected to the measuring device by means of a filter branch, such as a lowpass, which separates out the frequency range to be evaluated. It is beneficial to connect several filter branches for various frequency ranges to the multiplexer output. A measuring device can then be connected to each of these filter branches. In a preferred embodiment, the measuring device consists of a PLL-type tracking filter circuit which incorporates one circuit section for outputting a signal corresponding to the frequency to be determined and another circuit section for outputting a signal corresponding to the amplitude to be determined. The embodiment with a multiplexer allows in a simple manner to provide a further multiplexer input for electric fields influenced by capacitance of the organic substance. Furthermore, another input for fields generated within the organic substance is easily realized when using the multiplexer.

It is advantageous that the outputs of the individual measuring devices are connected to the corresponding inputs of a further multiplexer, the output of which is connected to a microcontroller, which, in a preferred embodiment, functions digitally and controls the adjusting elements for the individual field components of the field generated by the device in the delimited space.

Galvanic electrodes which can be placed against the conductive structure have proved to be good receiving devices for electric fields acting on the conductive structure by capacitance or for fields generated within the conductive structure. For example, such electrodes make it possible to derive signals corresponding to those of an electroencephalogram (EEG) from the organic structure of a living organism, and these signals can then be used as a criterion for adjustment of the frequency and amplitude of the aforementioned interference oscillation. The recommended type of receiving devices for magnetic fields acting on the conductive structure by inductance are coils, and for the magnetic constant field, such as the geomagnetic field acting within the delimited space, is a three-dimensionally recording magnetic flux meter or a Hall generator which, in a preferred embodiment, is temperature compensating.

BRIEF DESCRIPTION OF THE DRAWINGS

In the following, the invention will be explained in greater detail with the help of embodiments illustrated in the drawings.

In the drawing.

DESCRIPTION OF PREFERRED EMBODIMENTS

Figure 1:
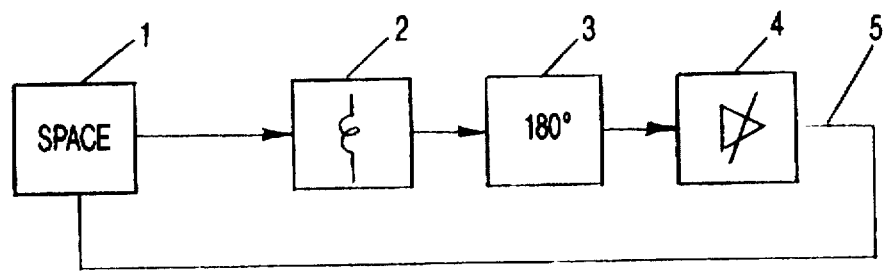
FIG. 1 shows a circuit diagram of an inventive device for eliminating the disruptive field in a room, for example, a living room.

Since the invention and the inventive devices are predominantly devices which are associated with influencing an organic substance by means of electric and magnetic fields, in the following the facts by which this association can be recognized shall initially be addressed.

For example, the body of a living organism roughly approximates a space filled with an electrolyte. This is especially true of the cranial region, which is basically a sphere filled with an electrolyte. Therefore, this space, and especially the cranial region, represents a type of isotropic antenna for electric and magnetic fields. The cerebral electrolyte in the cranial region contains the nerve cells with appendages (neurons). When the cerebral nerve cells are in active communication, they themselves become transmitters of electric and magnetic fields. The fields from the individual cells interfere with one another and accumulate to form aggregate fields which can be picked up and recorded electrically in the cranial region, for example, as an EEG (electro-encephalogram). Whenever localized stray external fields reach a critical intensity around the cranial region, they interfere with the fields generated within the brain. This can lead to amplitude or frequency modulation of the fields generated within the brain and give rise to biological feedback. The critical magnitude for such disruptive external fields, for which such effects have currently been determined, is approximately 0.4 microtesla for magnetic alternating fields and approximately 5 Volt/meters for electric alternating fields. Capacitively coupled fields act deep within the brain of a living organism, principally as dielectric currents and compensatory currents in the electrolyte, while inductively coupled and impressed fields can modify the aggregate field at practically all levels within the brain. Both the capacitive and inductive portions of such localized fields can give rise to biological feedback. In the course of several studies, it could be demonstrated that, for example, certain hormones, such as melatonin, which play an important role in sleep and therefore in the regeneration of a living organism as well as in providing a defence against cancer, can no longer be produced in adequate quantities at night. Furthermore, it has been found that the epiphysis (e.g. pineal body, pineal organ), which normally produces melatonin and two other hormones within the brain, is extremely sensitive to the geomagnetic field and further weak constant magnetic fields. The constant magnetic fields act in conjunction with the electric alternating fields to control the activities of enzymes (SNAT=serotonin-N-acetyl-transferase and HIOMT=hydroxindol-O-methyl-transferase) within the epiphysis. Both these enzymes react to electric and magnetic fields and specific frequencies thereof. The serotonin level is dependent, among other factors, on how much tryptophan, the precursor to serotonin, passes from food into the bloodstream for transport to the brain. Serotonin makes a major contribution to the emotional well-being of a living organism, particularly human beings. When during the day a great amount of light surrounds the living organism, the serotinin concentration in the brain is also great. During the night, this serotonin is transformed into melatonin, and the melatonin level peaks at approximately two a.m. Melatonin induces the creation of vasotonin which promotes restful sleep. The center for the entire process of hormone transformation and transfer is the epiphysis, which is a small outgrowth of the center of the brain.

Apparently, the epiphysis can "tap" into magnetic fields of the weakest magnitude and glean information from them.

This process has been well documented in animals such as fish, amphibians and birds. The ability of fields of relatively minimal magnitude to influence organisms is based on the fact that electromagnetic resonances, such as electron spin resonance and nuclear magnetic resonance, act as triggers. All such resonances require that a stationary magnetic field (the geomagnetic field or magnetic fields from iron masses, central heating pipes, etc.) acts on an atom, an electron or a molecule in conjunction with an electric or magnetic field of a specific frequency. For a human being, calcium ions ($Ca^{++}$), sodium ions ($Na^+$) and potassium ions ($K^+$) are particularly sensitive to resonance; these are the very ions which are most important in cells.

As mentioned above, the oscillating electric fields, which give rise to resonance and which act in conjunction with the geomagnetic field, are produced within the organism itself, mainly by nerve cells. This has been known for a long time, particularly in the case of the brain, which is an organ consisting almost exclusively of nerve cells, and can be measured as a radiating electric field (EEG) or a radiating magnetic field (MEG). When a living organism such as a human being is active during the day, this cerebral field, as the aggregate total of all active nerve cells, adopts frequencies from 20 to 25 Hertz. At night, when the organism is in deep sleep, it oscillates at frequencies well below 10 Hertz, and frequently as low as 3 Hertz. Further observations have shown that, during the day, these frequencies together with the natural geomagnetic field are within the frequency range of cyclotron resonances, while the low cerebral frequencies produced during the night (approximately 3 Hz to approximately 7 Hz) do not usually give rise to any resonances.

The analysis of the course of an EEG, which is known to be a unipolar or bipolar measurement derived from the potential fluctuations of the scalp, provides information about waves which can be classified by their speed, for example:

| | |
|---|---|
| Alpha waves = 9 to 12 (13) | fluctuations per second |
| Beta waves = 14 to 30 (50) | fluctuations per second |
| Delta waves = 0.5 to 3.5 | fluctuations per second |
| Theta waves = 4 to 7 | fluctuations per second |

The voltage of these waves is between 10 and 100 microvolts, with the voltage level being indirectly proportional to the speed of the wave.

Figure 6:
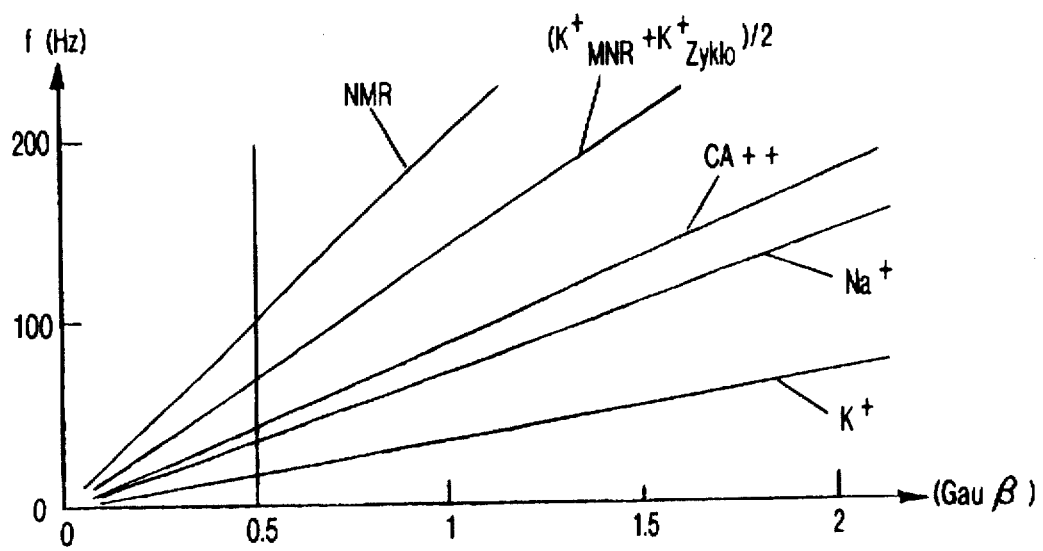
FIG. 6 shows a diagram to illustrate the known connection between the magnetic flux density measured in Gauss, and the frequency in Hertz at which ion resonance or NMR occurs, presenting as examples potassium, sodium and calcium ions.
Figure 9:
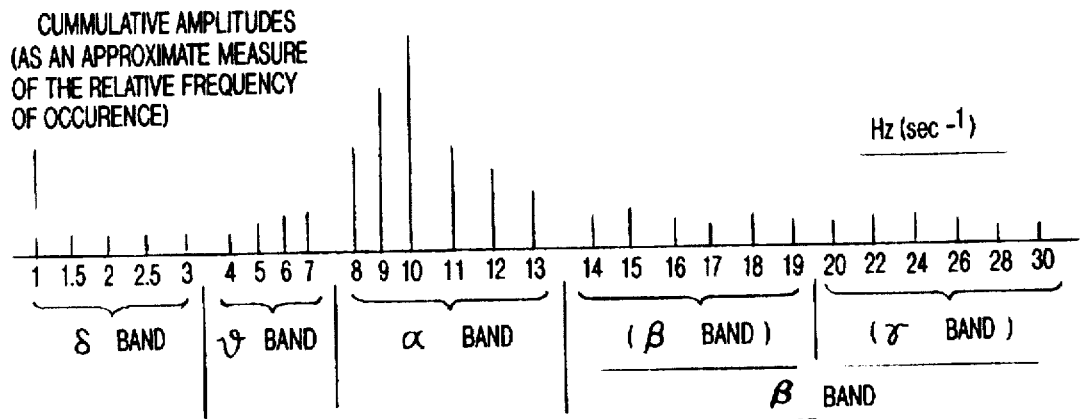
FIG. 9 shows a survey of the fields arising within the organic substance of a human being.

FIG. 6 shows a survey of cyclotron and NMR-type resonances determined by measurement, while FIG. 9 shows the survey of the EEG spectrum of a normal human being based on approximate amplitude and the corresponding frequency.

However, the normally occurring absence of resonances at nighttime and the related production of hormones, which production is essential for life, can be disrupted by localized fields. A cause of this may be a distortion of the effective constant magnetic field, such as the geomagnetic field, in such a way as to produce or form high or even low-intensity localized fields predominantly within the cerebral region. This can be induced principally by ferromagnetic metals such as the springs in a bed, metal shelves, radiators and devices operated using direct current. Furthermore, fields from electric power supply equipment give rise to stray magnetic fields which induce electromotive forces in the cerebral region; the strength of these forces can lie in the approximate region of, or higher than, the fields which naturally occur within the brain. This is especially true of areas surrounding high voltage power lines and practically all electric devices, especially domestic ones.

Accordingly, it is of great importance either to compensate the effect of the local fields within the delimited space and/or to support or create natural fields by means of fields or oscillations in the aforementioned frequency ranges (approximately 1 Hz to approximately 8 Hz or approximately 10 Hz to approximately 30 Hz).

The devices described in more detail below by means of exemplary embodiments provide a possibility for doing this.

FIG. 1 shows at 1 a delimited space, for example a living room, in which a magnetic 50 Hz oscillating field is generated by power supply lines. This oscillating field can also include harmonics. This field is picked up in the form of field components by a receiving device 2 which consists of coils, whereby the field components are oriented in accordance with a Cartesian system of coordinates (x, y, z). The amplitude and frequency of the x, y and z signals are determined in receiving device 2 or in a measuring device connected to this receiving device 2; the phase of the signals is inverted in an invertor 3 and the phase-inverted signals, separated according to the field components, are retransmitted by means of an amplifier 4, which is controllable with respect to the amplitude of its output signals and functions as a transmitter for the individual field components, and by means of coils (not shown) into the delimited space. In this process, both the amplitudes of the field components generated by the transmitter and the phases are adjusted so that the original 50 Hz field is almost fully compensated. The adjustment of the transmitter 4 with regard to the amplitude of the field components as well as the phase adjustment can be set manually or performed automatically by a closed-loop control circuit.

Figure 2:
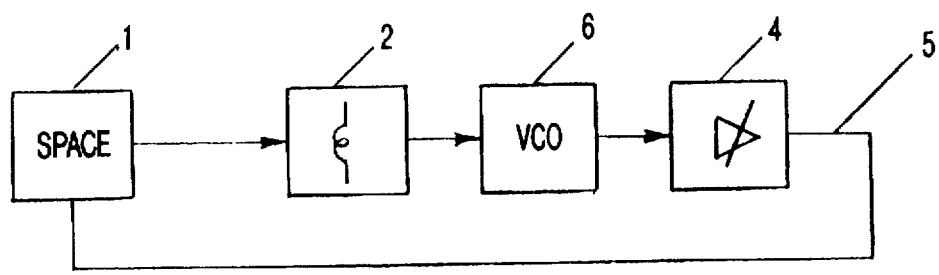
FIG. 2 shows a circuit diagram of an inventive device for inducing an oscillation field, for example in a bedroom, with the intention of promoting sleep.

FIG. 2 shows the principle of an inventive device, in which the frequency of the field components (x, y, z) radiated by a transmitter 6 into the delimited space are displaced to a lower frequency value. For example, if a localized 50 Hz field exists in 1, the radiated field components have a frequency of 46 Hz. As a result, a pulsating beat with a frequency of 4 Hz exists in space 1 in addition to the periodically compensating 50 Hz oscillations and 46 Hz oscillations. The beat or interference oscillation can be used for influencing the conductive substance within the delimited space in a targeted manner. This set-up is primarily intended for use in a bedroom, since the interference oscillation can have a favorable effect on promoting both the onset of sleep and the sleeping state.

An advantageous variant of the principle shown in FIG. 2 involves a heterodyne stage in which the field components picked up using the coil receiving device 2 are mixed with the oscillation of the localized transmitter 6, which can be, for example, a prior art VCO (voltage-controlled oscillator), whereby a lower-frequency sideband oscillation results which is radiated into the delimited space through a lowpass together with an oscillation which compensates the localized field, in accordance with FIG. 1.

Figure 3:
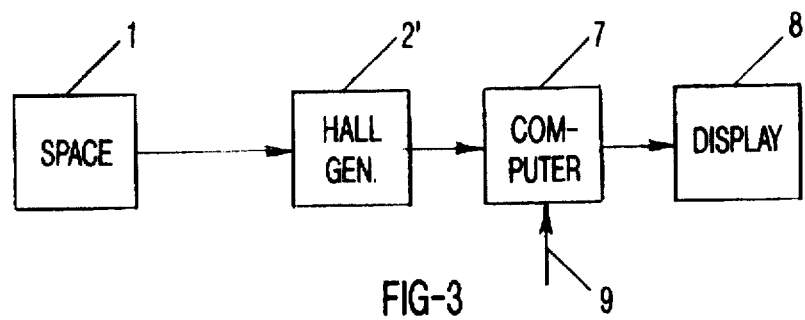
FIG. 3 shows a circuit diagram of a further inventive device for inducing an oscillation field, for example in a bedroom, with the intention of promoting sleep.

AS shown in the schematic circuit diagram in FIG. 3, it is possible to check for cyclotron and NMR resonances by using a magnetic flux meter or Hall generator 2' to measure the stationary constant magnetic field in the form of field components within the delimited space 1 and to evaluate these in a computer 7 using the alternating field components fed in through the input 9 which are picked up and/or generated in accordance with the examples presented, whereby the results are displayed on a display device 8.

Figure 4:
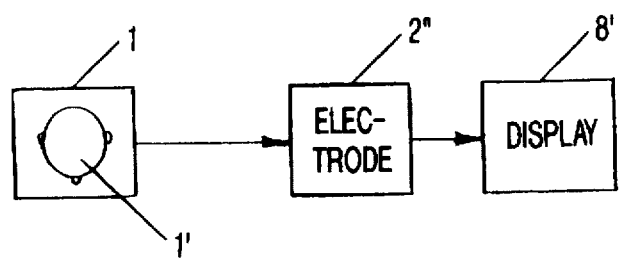
FIG. 4 shows a circuit diagram for picking up the fields arising or induced within an organic substance, which is also suitable for picking up the charge, induced in an organic substance by capacitance and occurring at the surface of the substance, and also renders induced fields measurable.

Signals which occur on the exterior of the body, for example, by pick-up of stray capacitive signals, can be measured using galvanic electrode receiving devices 2"

placed against the organic substance, as shown in FIG. 4. This is also the case for the fields generated or caused in the organic substance which can be measured as a type of EEG by applying the electrodes 2" to the skin of the body 1'.

Figure 5:
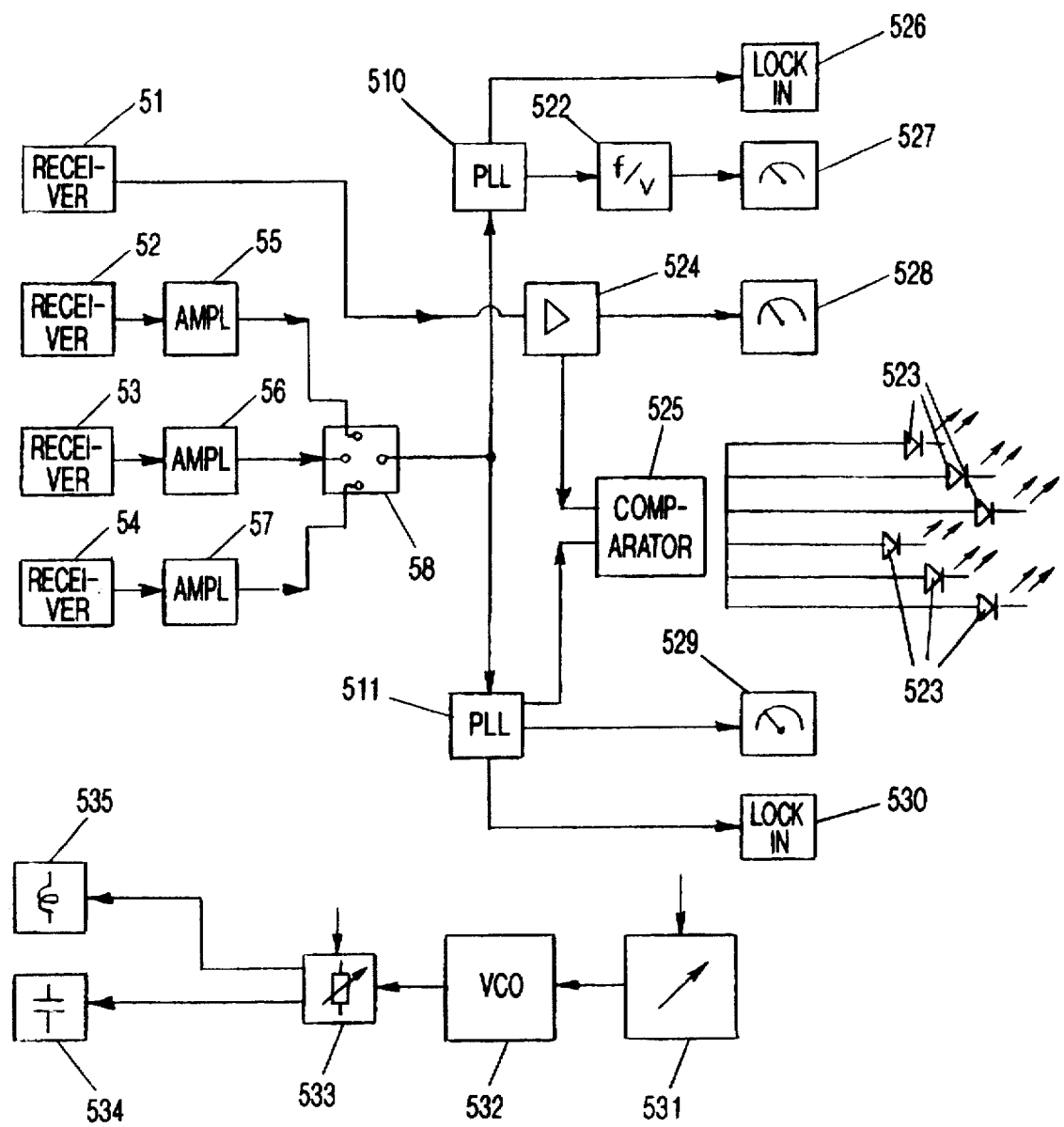
FIG. 5 shows an embodiment for compensating the 50 Hz alternating field which frequently occurs in homes.

In the device shown in FIG. 5, a Hall generator or a magnetic flux meter 51 is the receiving device for the stationary magnetic field, a galvanic hand-held electrode 52 is the receiving device for the localized alternating field capacitively induced on a body (not illustrated), an air core coil 53—which could be replaced by a magnetic flux meter in this example—is the receiving device for the localized magnetic field acting on the body in the delimited volume of space, and a galvanic electrode arrangement 54 is the receiving device for brain currents of the body. The receiving devices 51 and 52 pick up the respective field in three dimensions. For reasons of clarity, FIG. 5 only shows the circuit for only one of the three spatial field components picked up by each of the receiving devices. The signals of the receiving devices 52, 53 and 54 are fed through amplifiers 55, 56, 57 to the inputs of a multiplexer 58 which passes the signals on to two PLL circuits 510 and 511 for serial processing. The two PLL circuits are of conventional design and function as tracking filters in conjunction with a multiplexer for measuring the amplitude and frequency of the signals picked up by the receiving devices 52, 53 and 54. The PLL circuit 510 (522 and 526) determines the frequency value and supplies it to a display 527 by means of a frequency/voltage converter 522. The lock-in control is performed in circuit section 526. In the same way, the PLL circuit 511 (530) supplies the corresponding amplitude value to the display device 529. The module 530 is the corresponding lock-in control. A detailed description of the relevant PLL technology can be found, for example in Geschwinde, "Einführung in die PLL-Technik", published by Vieweg-Verlag, Braunschweig, 1978, e.g. chapters 2.2.1 and 2.2.2, so that a more detailed discussion is not deemed necessary.

Furthermore, the PLL circuit 511 which is used for measuring the amplitude also feeds a comparator 525, the second input of which receives the amplified output signal of the Hall generator 51 through an amplifier 524 which has low-pass characteristics. The output signal from the amplifier is also fed to a display 528 which enables the amplitude of the stationary magnetic field picked up by the Hall generator 51 to be determined precisely within the delimited space. The comparator 525 compares both signals fed to it and causes the corresponding light-emitting diode in an array 523 of light-emitting diodes to light up if it detects values which correspond to a cyclotron resonance and/or an NMR resonance. The top three light-emitting diodes shown in the drawing are for the cyclotron resonances of the ions of calcium, sodium and potassium, and the bottom three light-emitting diodes are for NMR resonances of the three elements.

VCO 532 generates the oscillation required to produce the counter field, whereby the oscillation is supplied via an amplitude controller in the form of an adjustable attenuator to a coil 535 which generates an alternating magnetic field in the delimited space and to a capacitive or galvanic electrode which generates an alternating electric field within the delimited space in accordance with the principle explained in connection with FIGS. 1 and 2. In this instance also, the figure only shows the circuit for one of the three field components of both fields in each case. Of course, the frequency/phase and amplitude adjustment of the transmitter could be performed manually using corresponding known adjustment elements. However, a self-adjusting method is more practical. Accordingly, the frequency of the VCO 532 can be compared with the frequency of the localized field by means of a comparator 531, whereby the resulting signal, which represents a measure of any possible frequency difference, is used as a control parameter for the VCO in a manner known per se. In the same way, the amplitude value of the local fields obtained using the appropriate PLL circuit can be used for adjusting the amplitude controller.

The VCO can either be exactly set to the concentration frequency of the localized alternating field, or it can be adjusted to a specified frequency value which is different from the concentration frequency of the localized alternating field, in order to create the interference oscillation as described above in connection with FIG. 2. Also, the VCO 532 can be replaced by a generator circuit, which, according to the alternative described in connection with FIG. 2, generates an exactly compensating oscillation and an additional oscillation serving as a replacement for the interference oscillation described there.

FIG. 6 presents a diagram describing the connection between the resonances (in Hertz) of the ions of calcium, sodium and potassium and the magnetic flux density (in Gauss). The three graph lines of the elements Ca, Na and K correspond to the cyclotron resonances of the ions of these elements. The others correspond to purely $K^+$NMR resonance and mixed resonance.

Figure 7:
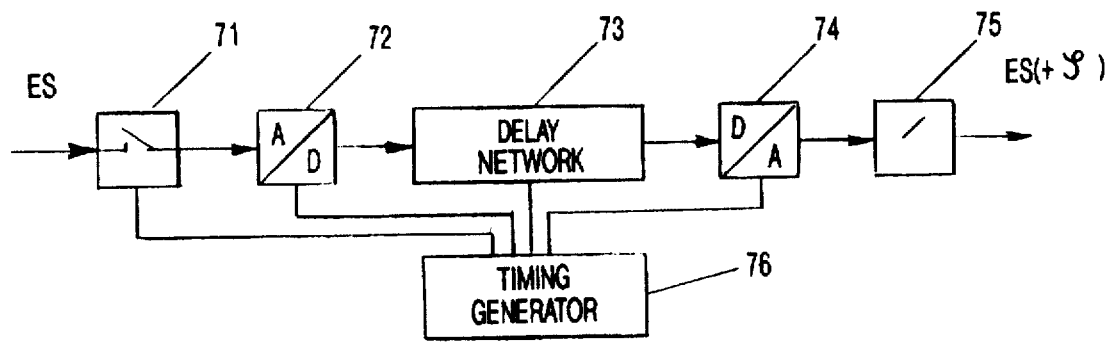
FIG. 7 shows a conventional circuit in communications transmission engineering for non-dispersion phase shifts, which can also be used for signal inversion in used for signal inventive devices.

FIG. 7 shows a schematic phase displacement circuit, which operates using digital technology and has been known since 1970. It is, for example, used in storage oscilloscopes for non-dispersion signal delay. The signal ES to be delayed is scanned by a sample 71. The individual amplitude samples in the scanning sequence are converted into a series of PCM signals in an analog-digital converter 72 and are then run through a digital delay network 73. At the output of the delay network 73, the sequence of PCM signals is converted back into a series of amplitude samples by a digital-analog convertor 74 and this series is then reformulated in a low-pass 75 which suppresses unwanted frequencies so that the original signal can be extracted as a continuous but time-delayed element. The time delay is determined by the timing frequency of the timing generator 76, as well as the number of storage cells which are positioned one after the other in the direction of transmission in the delay network 73. In a simplified version, both converters 72 and 75 can be dispensed with and the delay network can take the form of a chain of CCD-type charge transfer elements. Additionally, a "bucket bridge delay" circuit can also be used as an "analog phase displacer" in the form of an all-pass filter.

Figure 8:
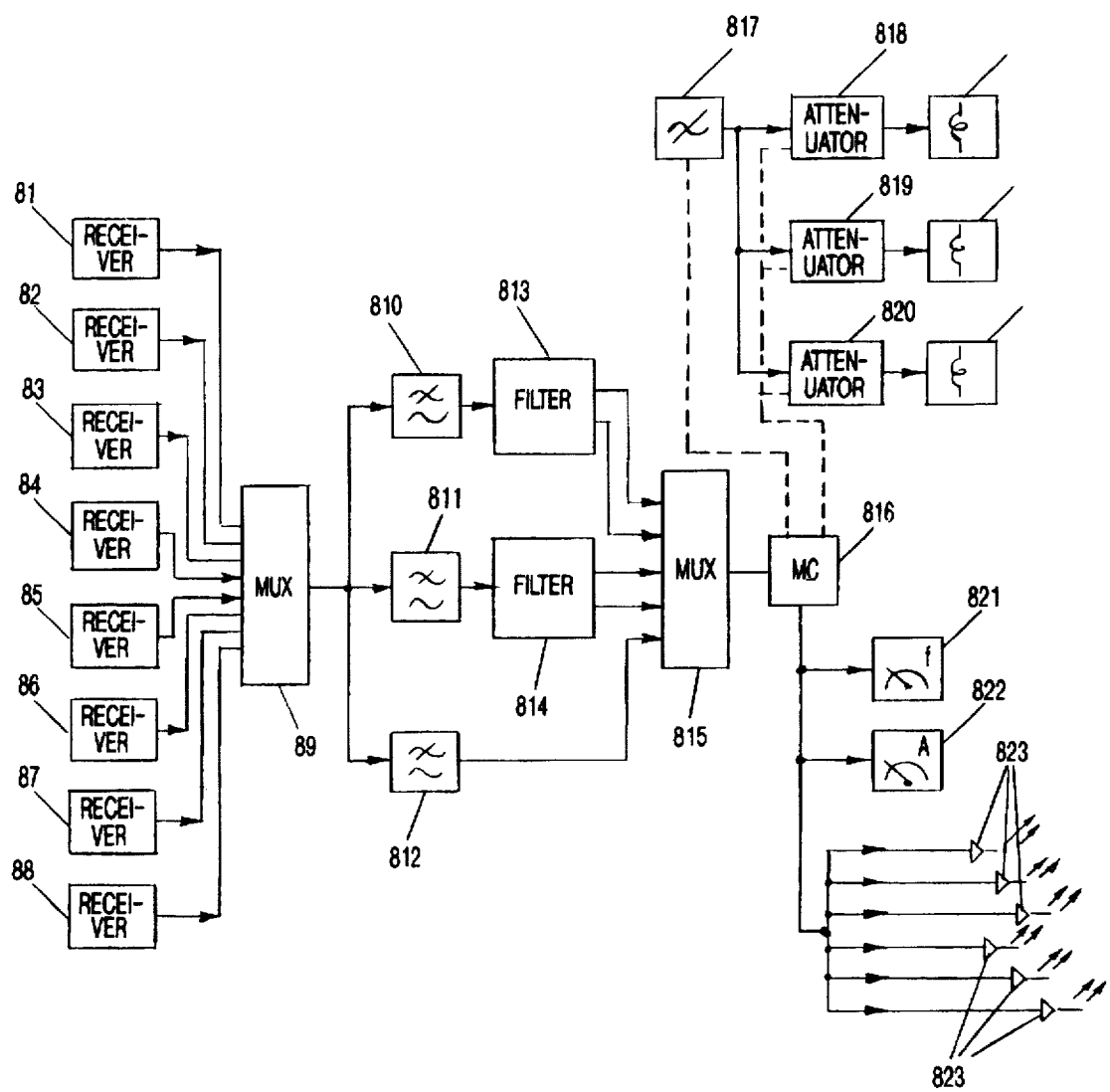
FIG. 8 shows a further embodiment of the invention for determining the magnetic field components of a constant magnetic field existing within a delimited space or of a magnetic alternating field, induced electric fields and the fields arising or induced within an organic substance located in the space

In the embodiment shown in FIG. 8, modules 81 to 88 are receiving units of the following allocation:

81 receiving unit for the x-component of the geomagnetic field, 82 receiving unit for the y-component of the geomagnetic field, 83 receiving unit for the z-component of the geomagnetic field, 84 receiving unit for the x-component of the localized alternating magnetic field, 85 receiving unit for the y-component of the localized alternating magnetic field, 86 receiving unit for the z-components of the localized alternating magnetic field, 87 receiving unit for the alternating electric field acting on the body of a human being by capacitive inductance, 88 receiving unit for the aggregate field (BEG) produced in the body of a human being, in particular in the brain.

The output signals of the receiving units are combined using a multiplexer 89 by means of chronological interweaving. The multiplexer 89 supplies three parallel branches which all have a low-pass filter on their input end for suppressing unwanted higher frequency elements which arise during sampling and which, given unfavorable phase conditions, could also cause self-excitation of the entire equipment. The concentration frequency of the localized alternating field to be compensated is assumed to be approximately 50 Hz. Furthermore, an oscillation lower than this frequency, along the lines of the interference oscillation described in FIG. 2, should be present with a frequency below 10 Hz, and the stationary magnetic field (geomagnetic field and any other constant magnetic fields) should be taken into consideration. A tracking filter 813 of the type described in FIG. 5 is provided for the 50 Hz field, and a low-pass 810 with a limit frequency of 50 Hz is connected upstream of this filter. A corresponding tracking filter with a low-pass filter 811 connected upstream of it is also provided for the alternating field which is of a lower frequency than the 50 Hz field, and the limit frequency of the low-pass filter 811 is approximately 10 Hz. A low-pass with a limit frequency of approximately 1 Hz is located in the third one of the parallel branches for the signal which corresponds to the stationary magnetic field. The PLL circuits of the tracking filters 813 and 814 operate in series to determine the amplitude and the frequency of the various fields, which are chronologically separated in each case in accordance with the three field components of the Cartesian system of coordinates (x, y, z). The results obtained from the outputs of the tracking filters 813 and 814 are supplied to the inputs of the multiplexer 815 together with the field components of the constant magnetic field which are fed through the low-pass 812, and the multiplexer 815 sends them to a microcontroller 816 for evaluation in serial form.

In this embodiment, oscillations are generated in the same way as shown in FIG. 5 with a VCO 817 which is frequency-adjustable by a control voltage. The frequency of the VCO 817 is adjusted by the microcontroller which for this purpose evaluates the signals received from the tracking filters 813 and 814 via the multiplexer 815. The transmitter coils x, y, and z are supplied from the VCO 817 via controllable attenuators 818, 819 and 820 and generate the compensating and/or interfering counter field in the delimited space. In turn, the attenuators and thus the amplitude values of the individual field components of the counter field are adjusted using the microcontroller 816 based on the signals fed to the microcontroller 816 through tracking filters 813, 814 and multiplexer 815. The control line for the VCO and the three attenuators are shown with dashed lines.

Since the microcontroller is additionally supplied with the field components of the stationary magnetic field and the EEG signals, possibly occurring resonances of the cyclotron or NMR type arising in the microcontroller can be evaluated and displayed using a display device 823, such as an array of light-emitting diodes. Also, the microprocessor 816 can be used for deriving a frequency display 821 and an amplitude display 822 for the localized alternating field and the other alternating fields, such as the counter field and the field of an interference oscillation.

The present invention is, of course, in no way restricted to the specific disclosure of the specification and drawings, but also encompasses any modifications within the scope of the appended claims.

I claim:
1. A device for influencing localized low-frequency electric and magnetic alternating fields acting on a conductive structure within a delimited space, said device comprising:
   a first receiving device for picking up the electric and magnetic fields as oriented electric and magnetic field components of a system of coordinates;
   a measuring device connected to said receiving device for determining amplitude, frequency, and orientation of the field components picked up with said receiving unit;
   a control member;
   a transmitter, connected to said control member and said control member connected to said measuring device, said transmitter comprising a device for generating a counter field within said delimited space;
   wherein said control member, said transmitter and said device for generating a counter field are adjustable with regard to frequency, magnitude and coordinate orientation of said counter field such that said counter field generated within the delimited space at least approximately compensates by interference the effect of the electric and magnetic alternating fields on the conductive structure;
   wherein said transmitter generates via said device for generating an oscillation field within said space, said oscillation field having a frequency lower than a frequency of said counter field.

2. A device according to claim 1, wherein said frequency of said oscillation field is between 1 Hz to 8 Hz.

3. A device according to claim 1, wherein said frequency of said oscillation field is between 10 Hz to 30 Hz.

4. A device according to claim 1, further comprising a frequency filter for limiting the effect of said frequency of said oscillation field on said field components.

5. A device according to claim 4, wherein said frequency filter comprises a low-pass filter.

6. A device according to claim 1, further comprising a loop circuit for monitoring at certain time intervals for a short period of time an adjustment of said control member according to predetermined frequency criteria and for decoupling said transmitter from said receiving device when said frequency criteria are fulfilled.

7. A device according to claim 1, further comprising:
   a second receiving device for determining the constant magnetic field of said electric and magnetic fields present within said delimited space according to magnitude and coordinate orientation; and
   a resonance-determining device for receiving signals from said first and second receiving device and for determining resonances present within said conductive structure.

8. A device according to claim 7, wherein said constant magnetic field comprises the geomagnetic field.

9. A device according to claim 1, further comprising galvanic electrodes for placing against the structure as a means for receiving electric fields capacitively acting on the structure.

10. A device according to claim 1, further comprising galvanic electrodes for placing against the structure as a means for receiving electric fields capacitively generated within the structure.

11. A device according to claim 1, wherein said receiving device comprises coils for receiving magnetic fields acting inductively on the conductive structure.

12. A device according to claim 1, wherein said receiving device comprises a magnetic flux meter for receiving the geomagnetic field acting within the delimited space.

13. A device according to claim 1, wherein said receiving device comprises a Hall generator for receiving the geomagnetic field acting within the delimited space.

14. A device according to claim 13, wherein said Hall generator comprises means for temperature compensation.

15. A device according to claim 1, wherein said receiving device acquires said field components in cartesian coordinates and comprises a first receiving unit for said electric field components and a second receiving unit for said magnetic field components, said device further comprising a first multiplexer with inputs and an output, wherein said first and second receiving units are connected to said inputs of said first multiplexer and wherein said output of said first multiplexer is connected to said measuring device.

16. A device according to claim 15, further comprising a filter branch connected between said output of said first multiplexer and said measuring device, said filter branch separating out the frequency range to be evaluated.

17. A device according to claim 16, wherein said filter branch comprises a low-pass filter.

18. A device according to claim 15, further comprising a plurality of filter branches for various frequency ranges and in addition to said measuring device a plurality of further measuring devices, wherein each said filter branch is connected to said output of said first multiplexer and to one of said measuring device and further measuring devices.

19. A device according to claim 15, wherein said measuring device comprises of a PLL-type tracking filter circuit comprising a circuit section for outputting a signal corresponding to the frequency to be determined and a circuit section for outputting a signal corresponding to the amplitude to be determined.

20. A device according to claim 15, wherein said multiplexer has a further input for receiving electric fields capacitively influenced by the organic substance.

21. A device according to claim 15, wherein said multiplexer has a further input for receiving electric fields generated within the organic substance.

22. A device according to claim 15, further comprising:
a second multiplexer with inputs and an output, wherein outputs of said measuring devices are connected to said inputs of said second multiplexer; and
a microcontroller, connected to said output of said multiplexer, for controlling adjusting elements for the individual field components of said counter field generated within said delimited space.

23. A device according to claim 22, wherein said microcontroller comprises a digital microcontroller.

24. A device for influencing localized low-frequency electric and magnetic alternating fields acting on a conductive structure within a delimited space, said device comprising:
a first receiving device for picking up the electric and magnetic fields as oriented field components of a system of coordinates;
a measuring device connected to said receiving device for determining amplitude, frequency, and orientation of the field components picked up with said receiving unit;
a control member;
a transmitter, connected to said control member and said control member connected to said measuring device, said transmitter comprising a device for generating a counter field within said delimited space;
wherein said control member, said transmitter and said device for generating a counter field are adjustable with regard to frequency, magnitude and coordinate orientation of said counter field such that said counter field generated within the delimited space at least approximately compensates by interference the effect of the electric and magnetic alternating fields on the conductive structure;
wherein said transmitter has a frequency displaced relative to a frequency of said electric and magnetic fields by such a frequency value that within said delimited space an interference oscillation of a relatively low frequency relative to a main frequency of said electric and magnetic fields is produced.

25. A device according to claim 24, wherein said interference oscillation is between 1 Hz to 8 Hz.

26. A device according to claim 24, wherein said interference oscillation is between 10 Hz to 30 Hz.

27. A device according to claim 24, further comprising a frequency filter for limiting the effect of said interference oscillation on said field components.

28. A device according to claim 27, wherein said frequency filter comprises a low-pass filter.

29. A device according to claim 24, further comprising a loop circuit for monitoring at certain time intervals for a short period of time an adjustment of said control member according to predetermined frequency criteria and for decoupling said transmitter from said receiving device when said frequency criteria are fulfilled.

30. A device according to claim 24, further comprising galvanic electrodes for placing against the structure as a means for receiving electric fields capacitively acting on the structure.

31. A device according to claim 24, further comprising galvanic electrodes for placing against the structure as a means for receiving electric fields capacitively generated within the structure.

32. A device according to claim 24, wherein said receiving device comprises coils for receiving magnetic fields acting inductively on the conductive structure.

33. A device according to claim 24, wherein said receiving device comprises a magnetic flux meter for receiving the geomagnetic field acting within the delimited space.

34. A device according to claim 24, wherein said receiving device comprises a Hall generator for receiving the geomagnetic field acting within the delimited space.

35. A device according to claim 34, wherein said Hall generator comprises means for temperature compensation.

36. A device according to claim 24, further comprising:
a second receiving device for determining a constant magnetic field of said electric and magnetic fields present within said delimited space according to magnitude and coordinate orientation; and
a resonance-determining device for receiving signals from said first and second receiving device and for determining resonances present within said conductive structure.

37. A device according to claim 36, wherein said constant magnetic field comprises the geomagnetic field.

38. A device according to claim 36, further comprising a means for adjusting said frequency of said interference oscillation and the power of said transmitter as a function of said constant magnetic field within said delimited space such that said interference oscillation in cooperation with said constant magnetic field fulfill the conditions for nuclear magnetic resonance of an organic substance.

39. A device according to claim 36, wherein said frequency of said interference oscillation and the power of said transmitter are adjustable as a function of said constant magnetic field within said delimited space such that said interference oscillation in cooperation with said constant magnetic field fulfill the conditions for a cyclotron resonance with ions.

40. A device according to claim 39, wherein said ions are selected from the group consisting of calcium ions, potassium ions and sodium ions.

41. A device according to claim 39, further comprising:
a second multiplexer with inputs and an output, wherein outputs of said measuring devices are connected to said inputs of said second multiplexer; and
a microcontroller, connected to said output of said multiplexer, for controlling adjusting elements for the individual field components of said counter field generated within said delimited space.

42. A device according to claim 41, wherein said microcontroller comprises a digital microcontroller.

43. A device according to claim 25, wherein said receiving device acquires said field components in cartesian coordinates and comprises a first receiving unit for said electric field components and a second receiving unit for said magnetic field components, said device further comprising a multiplexer with inputs and an output, wherein said first and second receiving units are connected to said inputs of said multiplexer and wherein said output of said multiplexer is connected to said measuring device.

44. A device according to claim 43, further comprising a filter branch connected between said output of said multiplexer and said measuring device, said filter branch separating out the frequency range to be evaluated.

45. A device according to claim 44, wherein said filter branch comprises a low-pass filter.

46. A device according to claim 43, further comprising a plurality of filter branches for various frequency ranges and in addition to said measuring device a plurality of further measuring devices, wherein each said filter branch is connected to said output of said multiplexer and to one of said measuring device and further measuring devices.

47. A device according to claim 43, wherein said measuring device comprises of a PLL-type tracking filter circuit comprising a circuit section for outputting a signal corresponding to the frequency to be determined and a circuit section for outputting a signal corresponding to the amplitude to be determined.

48. A device according to claim 43, wherein said multiplexer has a further input for receiving electric fields capacitively influenced by the organic substance.

49. A device according to claim 43, wherein said multiplexer has a further input for receiving electric fields generated within the organic substance.

* * * * *